United States Patent [19]

Hunt et al.

[11] 4,088,747
[45] May 9, 1978

[54] PHENOLIC AMINO-CARBOXYLIC ACID RADIOPHARMACEUTICALS

[75] Inventors: Frederick Charles Hunt, Oatley; John Gerald Wilson, Strathfield, both of Australia

[73] Assignee: Australian Atomic Energy Commission, Coogee, Australia

[21] Appl. No.: 655,034

[22] Filed: Feb. 3, 1976

[30] Foreign Application Priority Data

Feb. 19, 1975 Australia .............................. PC0655
Jul. 29, 1975 Australia .............................. PC2552

[51] Int. Cl.² ...................... A61K 27/00; A61K 43/00
[52] U.S. Cl. .................................. 424/1; 260/518 R; 424/9; 260/429.7
[58] Field of Search ............ 260/518 R, 518 A, 429.7; 424/1, 1.5, 9, 305, 313, 365, DIG. 6

[56] References Cited

U.S. PATENT DOCUMENTS

| Re. 23,905 | 12/1954 | Bersworth | 260/518 A |
|---|---|---|---|
| 2,624,757 | 1/1953 | Bersworth | 260/518 R |
| 3,509,208 | 8/1970 | Alburn et al. | 260/518 R |
| 3,749,556 | 8/1971 | Barak et al. | 424/1 |
| 3,833,590 | 9/1974 | Dazzi | 260/518 R |

FOREIGN PATENT DOCUMENTS

1,431,697 2/1966 France .............................. 260/518 R

*Primary Examiner*—Benjamin R. Padgett
*Assistant Examiner*—Christine M. Nucker
*Attorney, Agent, or Firm*—Ladas, Parry, Von Gehr, Goldsmith & Deschamps

[57] ABSTRACT

A radiopharmaceutical for use on animals including human beings comprises a metal chelate in which the chelating agent is a phenolic amino carboxylic acid or an alkali salt thereof, and the metal is a pharmaceutically acceptable radio isotope such as technetium-99m. The chelating agent may be advantageously an ethylenediamine carboxylic acid or its salt having a phenolic group at each end of the molecule such as EDDHA and HBED or alternatively the phenolic amino carboxylic acid or its salt may have a single phenolate group such as HBG or HBS. The pharmaceutical has a balance of lipo-solubility and water-solubility to permit hepatobiliary imaging.

10 Claims, No Drawings

PHENOLIC AMINO-CARBOXYLIC ACID RADIOPHARMACEUTICALS

The present invention relates to radiopharmaceuticals and more particularly to radioactive complexes which can be used as diagnostic pharmaceuticals to permit imaging of certain animal organs by scintigraphic means and assessing their functions.

More specifically, the invention is concerned with metal chelates in which the metal is a pharmaceutically acceptable radioactive isotope, the metal chelate being selected and designed so as to be distributed in a certain way when administered to an animal, whereby imaging of certain selected organs and assessment of their function can take place.

Radiopharmaceuticals have previously been made and used as imaging agents for investigating the function of organs in animals including human beings. Complexes of radioactive isotopes have been formed and used by administering the complex, usually intravenously, with the result that the material is carried by the bloodstream to locate preferentially but temporarily in some particular organ. By the use of suitable imaging equipment, the passage of the compound through the organ can be observed and deductions can be made as to whether the organ is functioning satisfactorily or has any defects.

Radiopharmaceuticals for use as imaging agents are known. After the administration of a dose, the passage of the material is imaged by using known scintigraphic apparatus. Certain body functions can be imaged by the use of radioactive complex formed from the known chelating agent ethylenediaminetetracetic acid (EDTA). EDTA is water-soluble and U.S. Pat. No. 3,466,361 describes the use of a technetium complex of EDTA for kidney imaging. However, this complex does not have use where lipo-solubility is necessary for imaging of certain organs to occur.

The present invention is concerned with the problem of providing new radioactive imaging agents which are lipo-soluble and which could be administered to animals including human beings. There is need for new imaging agents to be provided which have low toxicity, a reduction in the type and level of any side effects, convenience of use, greater economy, rapid preferential location in animal and a high degree of preferential location.

The present invention is particularly directed to the provision of novel radiopharmaceuticals for imaging hepato-billary function.

The present invention provides such a radiopharmaceutical as a metal chelate in which the metal is a pharmaceutically acceptable radio isotope for an animal and the chelating agent is a phenolic aminocarboxylic acid or an alkali metal salt thereof.

Embodiments of the invention include material derived from a chelating agent having a single phenolate group although as will be explained hereinafter it appears that better results are derived from the use of a chelating agent which is an ethylenediamine carboxylic acid or its salt, which has a phenolic group at each end of the molecule.

A particularly important group of chelating agents for use in embodiments of the present invention is the group consisting of or based on the following compounds:

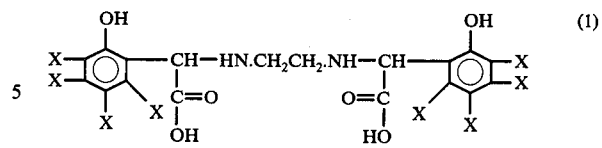

where X is hydrogen, a halogen or an alkyl group, this compound being known as ethylenebis (α-imino-o-hydroxyphenylacetic acid) referred to as EDDHA:

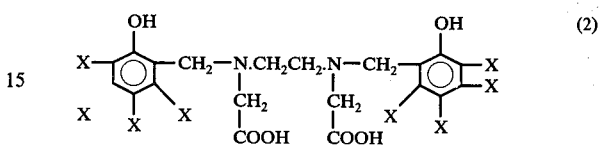

wherein X is hydrogen, halogen or an alkyl group, this compound being known as N,N-di (2-hydroxybenzyl) ethylene-diamine-N,N-diacetic acid and referred to hereinafter as HBED:

(3) Hydroxy benzyl glycine hereinafter referred to as HBG and having the formula:

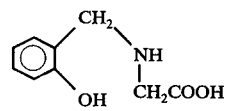

(4) Hydroxyl benzyl sarcosine, hereinafter referred to as HBS and having the formula:

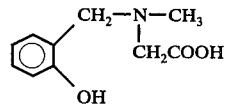

The invention is preferably used with the metal being technetium-99m which is known to be an acceptable radio isotope for pharmaceutical uses. Indium 113m has also been successfully tested, but technetium is preferred.

The present invention is primarily concerned with the provision of an imaging agent for investigation of hepatobiliary function in animals including human beings. According to the invention, a suitable metal radio isotope is chosen and is applied to a chelating agent selected for its capacity to form an effective metal chelate which has a good balance of aqueous and lipid solubility and will preferentially locate both rapidly and with a high degree of preference in the liver of an animal for excretion along the common bile duct whereby the passage of the material with time can be monitored by imaging with conventional scintigraphic apparatus for the purpose of determining the function of the liver and bile duct. It is known that the liver has the capacity to remove fat soluble components and thus liposolubility is required, but in order to best administer a metal chelate embodying the invention, it should be water soluble so as to permit injection into the blood stream whereby rapid results can be obtained.

In preferred embodiments of the invention, the metal chelate is formed from a substituted derivative of the chelating agent. Advantageously the derivative is ethylene-bis-(α-imino-o-hydroxyphenylacetic acid) (EDDHA).

One particular derivative to be used in an important embodiment of the invention is ethylene-bis-(α-imino-2-hydroxy-5-chlorophenyl acetic acid), although other halogen substituted derivatives are also useful.

It has been found that embodiments of the invention can be particularly useful for use as an imaging agent for observing the morphology and function of organs such as the liver and gall bladder in animals. It is thought that at least some embodiments of the invention may be particularly useful in humans.

There is a great need for imaging agents which will permit organs such as the gall bladder to be visualised.

It is considered that embodiments of the invention may be particularly advantageous in permitting a convenient imaging agent to be provided, the agent having an acceptably low toxicity and an advantageously high level of preferential location at an advantageous rate thereby permitting rapid and efficient diagnosis to be carried out with high levels of safety.

Particularly when the metal chelate is formed from technetium-99m with the chelating agent being EDDHA or HBED, it is thought that a surprisingly high degree of preferential location at a rapid rate is achieved thereby permitting rapid imaging to occur with low toxicity and low side effects in the material, the rapid and highly preferential location facilitating very small radioactive doses to be included in the material.

The manner in which technetium chelate embodying the invention is formed is not fully understood, but it is thought that each molecule of chelating agent has a technetium atom which is bonded to the chelating agent through a plurality of bonds. The nature of the bonding is not understood but it is thought that in the case of EDDHA and HBED the bonding would involve any two or all of the following: the two nigrogen atoms, the two hydroxy groups and the two carboxylic acid groups.

It is thought that the chelating agent has a high lipid solubility as a result of the substituted phenolic ring structures in the molecule and it is this lipid solubility which results in the liver functioning to excrete the complex. Thus, technetium is temporarily preferentially located in the liver before passing to the gall bladder and duodenum.

Another aspect of the invention consists in a method of producing a metal chelate as described in any one of the forms mentioned above, characterised by adding a quantity of radionuclide to a tin (II) complex of the chelating agent, controlling the pH of the mixture and holding the mixture for a length of time sufficient to produce the desired complex.

The present invention is useful in a method of treating animals in which the examination step comprises administering a pharmaceutical complex according to the first aspect of the invention or made according to the second aspect of the invention and observing the resultant manner in which the complex is distributed in the animal by the use of scintigraphic apparatus.

One of the preferred chelating agents to be used according to the present invention is EDDHA compound the preparation of which has been reported in U.S. Pat. No. 2,824,128.

A large number of EDDHA compounds can be made which can be useful in the present invention and the following list is given by way of example:
ethylene-bis-(α-imino-o-hydroxynaphthyl acetic acid)
ethylene-bis-(α-imino-2-hydroxy-3-chlorophenyl acetic acid)
ethylene-bis-(α-imino-2-hydroxy-5-chlorophenyl acetic acid)
ethylene-bis-(α-imino-2-hydroxy-5-iodophenyl acetic acid)
ethylene-bis-(α-imino-2-hydroxy-3,5-dibromophenyl acetic acid)
ethylene-bis-(α-imino-2-hydroxy-3,5-dichlorophenyl acetic acid)
ethylene-bis-(α-imino-2-hydroxy-5-methylphenyl acetic acid)
ethylene-bis-(α-imino-2-hydroxy-3,5-dimethylphenyl acetic acid)
ethylene-bis-(α-imino-2-hydroxy-5-tertiarybutylphenyl acetic acid)
ethylene-bis-(α-imino-o-hydroxyphenyl acetic acid)

For the purpose of illustration examples will now be given of the production of metal chelates embodying the invention.

EXAMPLE 1

1 ml of a normal saline or aqueous solution containing technetium-99m in the form of pertechnetate was added to a preformed complex made by the addition of 250 μg to 1 mg of $SnCl_2.2H_2O$ to 15 mg of ethylene-bis-(α-imino-2-hydroxy-5-chlorophenyl acetic acid) in 5 ml of $H_2O$ at pH 8–9. The solution was stirred for 5–10 minutes, and finally the product was filtered through a membrane to sterilise the product.

EXAMPLE 2

1 to 2 ml of sodium pertechnetate was added to a preformed, sterile, freeze-dried complex containing 3 mg of ethylene-bis-(α-imino-2-hydroxy-5-chlorophenyl acetic acid) and 50–200 μg of $SnCl_2.2H_2O$. The resultant solution is ready for injection.

Other examples of the invention may be based on chelating agents of the HBED type, examples of which are as follows:
N,N'-bis-(2-hydroxy-3-chlorobenzyl)ethylenediamine diacetic acid
N,N'-bis-(2-hydroxy-5-chlorobenzyl)ethylenediamine diacetic acid
N,N'-bis-(2-hydroxy-3,5-dibromobenzyl)ethylenediamine diacetic acid
N,N'-bis-(2-hydroxy-3,5-dichlorobenzyl)ethylenediamine diacetic acid
N,N'-bis-(2-hydroxy-5-iodobenzyl)ethylenediamine diacetic acid
N,N'-bis-(2-hydroxy-5-methylbenzyl) ethylenediamine diacetic acid
N,N'-bis-(2-hydroxy-3,5-dimethylbenzyl) ethylenediamine diacetic acid
N,N'-bis-(2-hydroxy-5-tertiarybutylbenzyl) ethylenediamine diacetic acid
N,N'-bis-(2-hydroxy-benzyl) ethylenediamine diacetic acid
N,N'-bis-(2-hydroxy-benzyl) ethylenediamine diacetic acid Specific examples will now be given for further illustration.

EXAMPLE 3

1 ml of a normal saline or aqueous solution containing technetium-99m in the form of pertechnetate was added to a preformed complex made by the addition of 250 μg to 1 mg of $SnCl_2 2H_2O$ to 15 mg of N,N'-bis-(2-hydroxy- 5-chlorobenzyl) ethylenediamine diacetic acid in 5 ml of H₂O at pH 8-9. The solution was stirred for 5-10 minutes, and finally the product was filtered through a membrane to sterilise the product.

EXAMPLE 4

1 to 2 ml of sodium pertechnetate was added to a preformed sterile, freeze-dried complex containing 3 mg of N,N'-bis-(2-hydroxy-5-chlorobenzyl) ethylenediamine diacetic acid and 50-200 μg of SnCl₂ 2H₂O. The resultant solution is ready for injection.

Tests have been conducted on animals; the product of each of the examples given above was administered in a pharmaceutical dose and useful images were obtained showing initially the preferential localisation of the complex in the liver and subsequent advance of the complex to the gall bladder and with the passage of further time the images showed passage of the material through the duodenum.

The formation of EDDHA, HBED, HBG and HBS are known and described in the following publications:

EDDHA: U.S. Pat. No. 2,824,128 — Inventors M. Dexter and R. J. Cranston.

HBED: British Pat. No. 843,000 — Applicant - Geigy A. H.

HBG and HBS: Czechoslovakian Pat. No. 94,067 — Inventors — J. Korbl and V. Svoboda.

We claim:

1. A radiopharmaceutical for imaging hepatobiliary function comprising a lipo-soluble metal chelate in which the metal is a pharmaceutically acceptable radio isotope for an animal and the chelating agent is selected from the group consisting of an ethylene diamine di(hydroxy phenyl carboxylic acid), a salt thereof, a di(hydroxy benzyl) ethylene diamine dicarboxylic acid and a salt thereof.

2. A radiopharmaceutical as claimed in claim 1, wherein the chelating agent is selected from the group consisting of

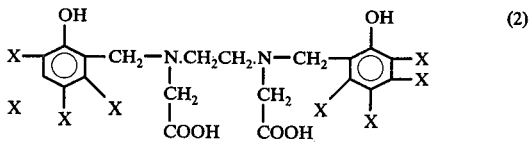

wherein X is hydrogen, a halogen or an alkyl group,

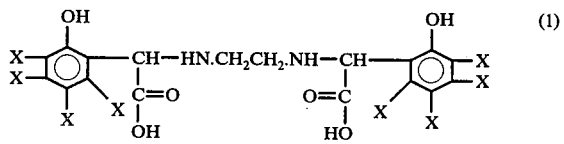

wherein X is hydrogen, a halogen or an alkyl group,
(3) an alkali metal salt of compound (1) above and
(4) an alkali metal salt of compound (2) above.

3. A radiopharmaceutical for imaging hepatobiliary function comprising a lipo-soluble metal chelate in which the metal is a pharmaceutically acceptable radio isotope for an animal and the chelating agent is a phenolic amino-carboxylic acid or a salt thereof said chelating agent having a single phenolic group, having a balance of both lipo-soluble and water-soluble properties.

4. A radiopharmaceutical as claimed in claim 3, wherein the chelating agent is selected from the group consisting of hydroxybenzyl glycine, hydroxybenzyl sarcosine, an alkali metal salt of hydroxybenzyl glycine and an alkali metal salt of hydroxybenzyl sarcosine.

5. A radiopharmaceutical as claimed in claim 4, wherein the chelating agent has alkyl or halogen substituents in the phenolic ring thereof.

6. A radiopharmaceutical as claimed in claim 2, wherein the chelating agent is ethylene-bis (α-imino-2-hydroxy-5-chlorophenyl acetic acid).

7. A radiopharmaceutical as claimed in claim 4, wherein the chelating agent is selected from the group consisting of N-(o-hydroxybenzyl)glycine and N-(o-hydroxybenzyl)sarcosine.

8. A radiopharmaceutical as claimed in claim 2, wherein the radio isotope is technetium-99m, and the radiopharmaceutical is a complex of stannous tin.

9. A radiopharmaceutical as claimed in claim 2, wherein the chelating agent has halogen substituents in the phenolic ring thereof.

10. A radiopharmaceutical as claimed in claim 9, wherein said halogen substituent is bromine.